United States Patent [19]

Paysan et al.

[11] Patent Number: 5,146,623
[45] Date of Patent: Sep. 15, 1992

[54] SAFETY SPECTACLES AGAINST LASER RADIATION

[75] Inventors: Heinz-Wilhelm Paysan, Aalen-Waldhausen; Wolfgang Grimm, Heidenheim; Hermann Schurle, Aalen; Hans Gaiser, Reutlingen; Heinz Gutbrod, Leonberg, all of Fed. Rep. of Germany

[73] Assignee: Carl-Zeiss-Stiftung, Heidenheim, Fed. Rep. of Germany

[21] Appl. No.: 573,632

[22] Filed: Aug. 24, 1990

[30] Foreign Application Priority Data

Aug. 26, 1989 [DE] Fed. Rep. of Germany ... 8910235[U]

[51] Int. Cl.⁵ .............................................. A61F 9/00
[52] U.S. Cl. ............................................ 2/12; 2/432; 2/449; 2/451; 351/44
[58] Field of Search .............. 2/11, 12, 13, 432, 439, 2/448, 449, 450, 451; 351/44, 45, 47, 49, 163, 117

[56] References Cited

U.S. PATENT DOCUMENTS

| D. 112,976 | 1/1939 | Brunetti | 2/13 |
|---|---|---|---|
| 1,650,576 | 11/1927 | Welsh | 351/117 |
| 3,519,339 | 7/1970 | Hutchinson et al. | 351/44 |
| 3,649,106 | 3/1972 | Hirschmann, Jr. | 351/117 |
| 4,271,538 | 6/1981 | Montesi et al. | 2/439 |
| 4,462,661 | 7/1984 | Witt | 2/432 |
| 4,472,035 | 9/1984 | Takamura et al. | 351/117 |
| 4,703,522 | 11/1987 | Schürle et al. | 2/432 |
| 4,835,796 | 6/1989 | Wiedner | 351/44 |
| 4,868,930 | 9/1989 | Blackstone | 2/439 |
| 4,976,530 | 12/1990 | Mackay et al. | 2/13 |

FOREIGN PATENT DOCUMENTS

| 753789 | 3/1967 | Canada | 2/449 |
|---|---|---|---|
| 1308587 | 2/1973 | United Kingdom . | |

OTHER PUBLICATIONS

"Laser-Gard" Anti-Laser Safety Goggles from Glendale.

Primary Examiner—Werner H. Schroeder
Assistant Examiner—Michael A. Neas

[57] ABSTRACT

A safety spectacles against laser radiation has a first frame part which is of integral construction and in which shields are integrated, which cover the area between the frame and the spectacle-wearer's face. This frame part is also drawn over the spectacle-wearer's temple area and forms temple plates. Fitted pivotably to these temple plates are side arms which are each integrated in a further plate which forms the continuation of the associated temple plate.

15 Claims, 4 Drawing Sheets

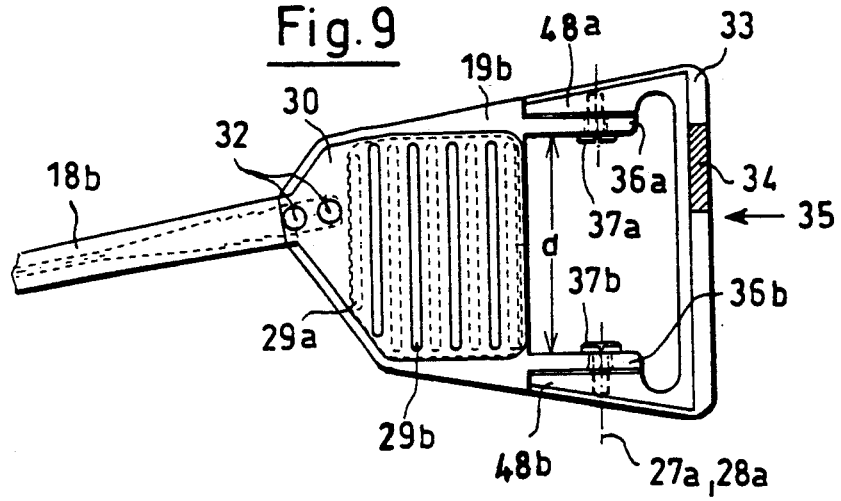
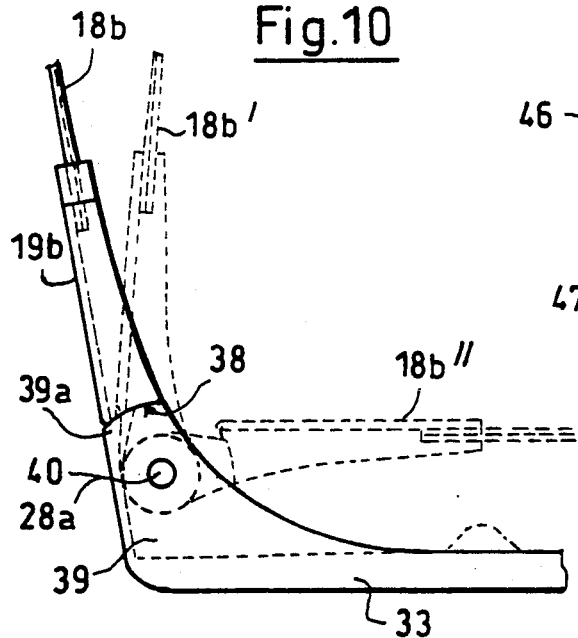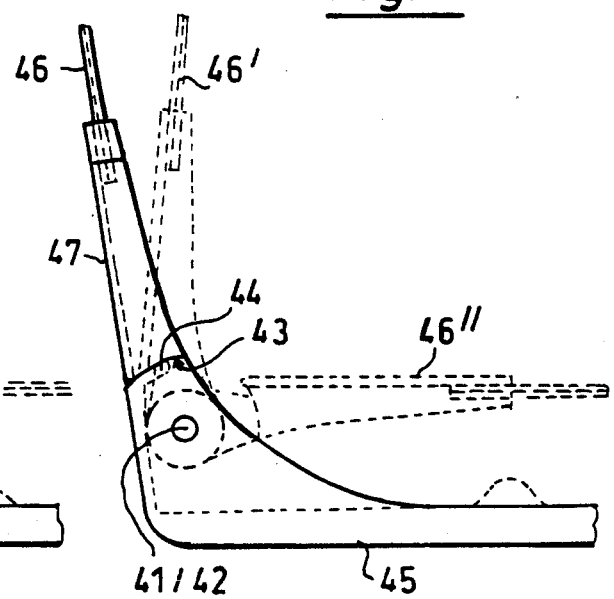

SAFETY SPECTACLES AGAINST LASER RADIATION

The present invention relates to safety spectacles to protect the eyes against laser radiation, which consist of protective filters and a spectacle frame serving to accommodate said filters and being provided with side arms.

BACKGROUND OF THE INVENTION

Safety spectacles of this type must be worn when working with lasers ranging from the hazard category 3b in order to protect the eyes from harmful radiation. In this case it is essential for the safety spectacles to protect the user's eyes not only reliably from radiation which comes essentially from the front but such that radiation arising from other directions is also kept away from the eyes.

To do so, frames are used such as are known, for example, from DE-AS 2,062,829 (which corresponds to British Patent Specification 1,308,587). In each temple area, these frames have a side shield connected to a side arm, which side shield rests on the associated eye edge of the frame in the open state. Frames of this type do not protect the areas above and below the eye edge, and there is a risk that the side shield does not rest closely on the associated eye edge of the frame and thus a gap occurs in the critical area.

German Utility Model 8,532,493 (which corresponds to U.S. Pat. No. 4,703,522) discloses safety spectacles against laser radiation, in which, in addition to temporal shields, shields are also provided in the upper frame area, which shields cover the area up to the spectacle-wearer's forehead. Here, too, there is the risk that a gap will form between side shield and eye edge of the frame; additionally, areas on the lower edge of the frame are not shielded.

These known frames are based on the customary, so-called work safety spectacles, on the frame of which the necessary shields are fitted. This makes these frames relatively expensive.

U.S. Pat. No. 4,527,291 discloses safety spectacles on which the side arms are attached to the spectacle frame from the outside. This type of side-arm attachment results in edges, which permit an undesired tearing-off of the safety spectacles. In addition, there are large uncovered areas between spectacle frame and spectacle wearer's face.

Recently the safety spectacles against laser radiation L-04 made by Laser-Vision GmbH have been available on the market, in which safety spectacles the frame extends temporally into the temple area and, only there, bears hinges for the pivotable attachment of the side arms. In this frame, transparent side shields, provided with protective filters, and shields on the top edge of the frame, are provided. Since all the shields are attached separately on one basic frame, this frame is also relatively expensive.

So-called basket frames for safety spectacles against laser radiation are also know. These frames are similar in their construction to diving goggles, for example German Patent Specification 3,616.253 (which corresponds to U.S. Pat. No. 4,835,796). The frame part surrounding the eye frames consists of soft elastic material and completely covers the area between the protective filters and the user's face. Basket frames of this type are usually used for visitors or for spectacle-wearers since they can be worn over the normal prescription frame. The basket frames mentioned do not have any side arms; they are held on the wearer's head by an elastic band.

The present invention does not relate to basket frames and the latter are also expressly excluded from protection.

OBJECT AND STATEMENT OF THE INVENTION

The object of the present invention is rather to provide safety spectacles against laser radiation that are fitted with side arms in such a way that said safety spectacles provide the greatest possible safety together with optimum wearing comfort.

This object is achieved according to the invention by a frame for safety spectacles against laser radiation that has the following features:

- protective filters for protecting the eyes against laser radiation, and
- a spectacle frame serving to accommodate said protective filters and provided with moveable side arms,
- wherein said frame is of integral construction and has in one cross section the form of a dish that is open towards a spectacle wearer's face;
- said frame has an inner, a front, a top and a bottom surface;
- said protective filters are inserted in said front surface of said frame,
- said top and said bottom surfaces cover an area as far as the spectacle wearer's face,
- said frame has sides that extend temporally into the spectacle wearer's temple area,
- said sides form a temple plate in each case,
- said temple plate has an inside and a first hinge part attached on said inside for pivotable attachment of one of said side arms,
- each of said side arms has a side arm plate,
- said side arm plate has an inside and forms a continuation of said temple plate when said side arm is at least partly open,
- each of said side arms has an end portion facing said temple plate, and
- a second hinge part, pivotable with said first hinge part, is integrated in the inside of said end portion of said side arm plate.

This frame has the advantage that the frame part accommodating the protective filters is of integral construction and, consequently, can be produced inexpensively. This frame part reliably shields the area between the frame and the wearer's face and also forms side shields in the temple area, i.e. it offers protection from harmful radiation which can arise from the front, from above or below and from the side. Due to the fact that the hinges are only fitted on the ear-side end of the side shields, there is also no risk that gaps will form in the critical area during movements of the side arms.

The side arms are fitted via hinges which are arranged in the interior of the frame, each side arm being integrated in a plate which forms the continuation of the associated side shield of the first frame part. By this means, a long, smooth side shield results, seen from the outside, which side shield is only interrupted by a separation joint.

The described embodiments include the following additional inventive features:

said temple plate and said side arm plate are separated at a separation joint and have walls at said separation joint with surfaces slopped over an entire wall thickness in such a way that said sloping surfaces rest on each other when said side arm is at least partly open. This construction of the separation joint prevents a gap, which would allow radiation through, from forming during slight movements of the side arms.

Each of said side arms is provided with a metal insert. It is achieved by means of the metal insert that the side arms bend and, consequently, can be adapted to the shape of the spectacle-wearer's head.

The first, integrally constructed frame part can be produced from lightweight metal, preferably from aluminum. A further expedient material has proved to be the plastic available under the trade name "Grilamid" which is used in a glass fiber reinforced form for the first frame part. The plastic "Grilamid", for example, is also used advantageously for the spectacle side arms, however without glass fiber reinforcement, and a metal insert is inserted.

When using the described plastic, with the safety spectacles against laser radiation according to the invention, a protection category better than 7A can be achieved for use with UV lasers. A similarly high protection category can also be achieved for the use of $CO_2$ lasers if the frame consists of aluminum.

It is advantageous if there are ventilation slits in the side arms. These ventilation slits are advantageously designed in such a way that no laser radiation can penetrate them into the area between the laser safety spectacles and the spectacle-wearer's face. An expedient design of the hinge is one in which said hinge parts have a pivot point that lies inside of said separation joint.

The side arm end pointing toward the temple plate should have a rounding, the center of the radius of which coincides with the pivot point of the hinge. Specifically, said hinge parts have a center of pivoting, and a circular sliding surface with a center of radius that coincides with said center of pivoting, and said hinge is provided between said side arm plate and said spectacle frame. Said center of pivoting is located in the area of said temple plate.

Furthermore, it is advantageous to perform the attachment of the side arms to the temple plate of the dish with the protective filters in the upper and lower area of this temple plate. Specifically, said second hinge part comprises two hinge members formed on said inner side of said side arm plate for attaching said side arm plate to said temple plate. Said hinge members are arranged in upper and lower areas of said side arm plate. The temple plate advantageously has in the pivoting area of the side arms a lip-shaped extension. Specifically, said spectacle frame has an interior, and a lip-like extension is formed in said frame interior in the region of said sloping surface in space not covered by said hinge parts.

DESCRIPTION OF THE DRAWINGS

The invention is described in greater detail below with reference to FIGS. 1-11 of the attached drawings which illustrate exemplary embodiments and in which:

FIG. 9 shows a side arm in side view;

FIG. 10 shows a hinge area in section, seen from above.

FIG. 11 shows a hinge area in section, seen from above.

DETAILED DESCRIPTION OF PREFERRED EMBODIMENTS

Figure 1:
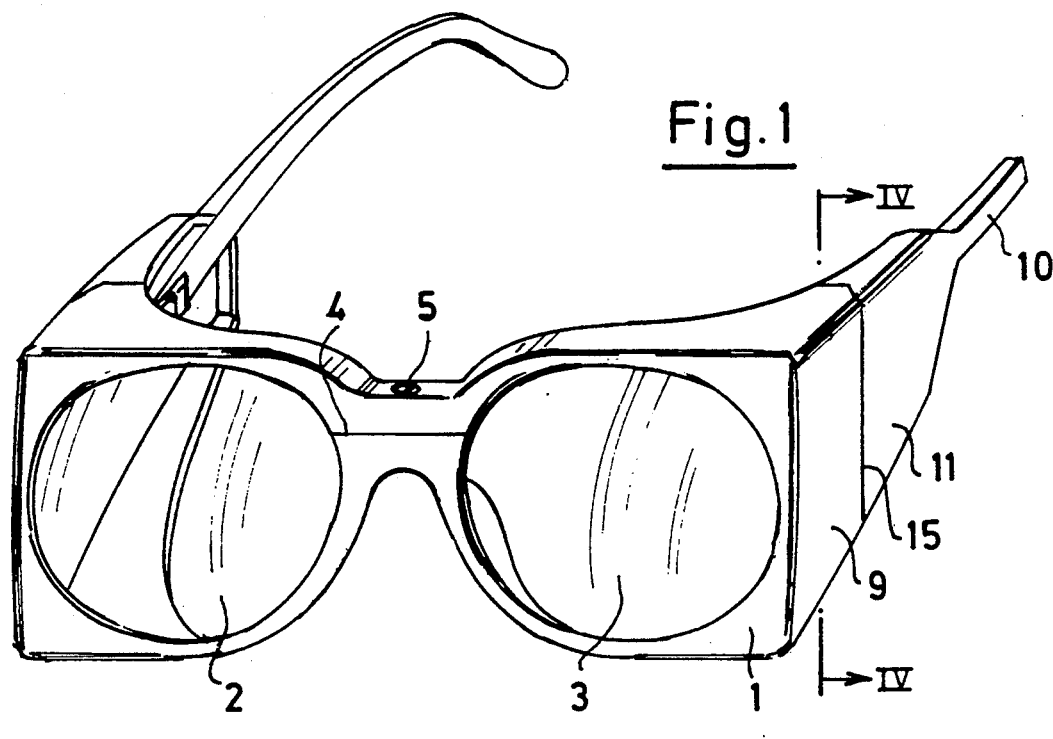
FIG. 1 shows a perspective illustration of safety spectacles against laser radiation.

In FIG. 1, the first frame part of the safety spectacles against laser radiation is denoted as (1). This frame part is of integral construction and bears the protective filters (2 and 3). To insert the protective filters (2, 3), the frame part (1) can be split at (4). After insertion of the protective filters (2, 3), a screw (5) serves for radiation-tight closing of the gap (4).

Figure 2:
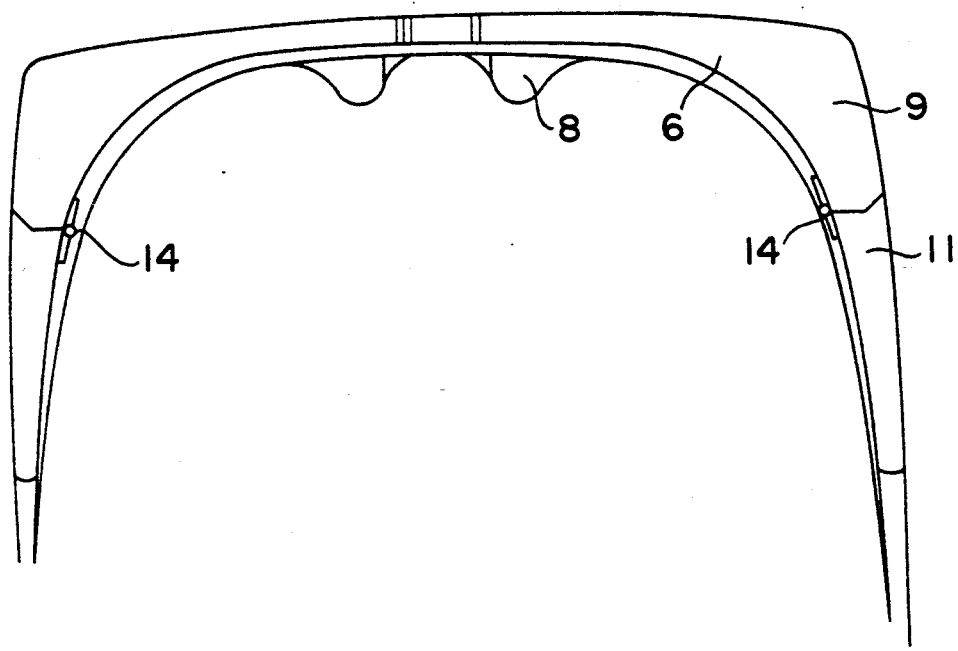
FIG. 2 shows the view of the safety spectacles against laser radiation according to FIG. 1 from above.
Figure 3:
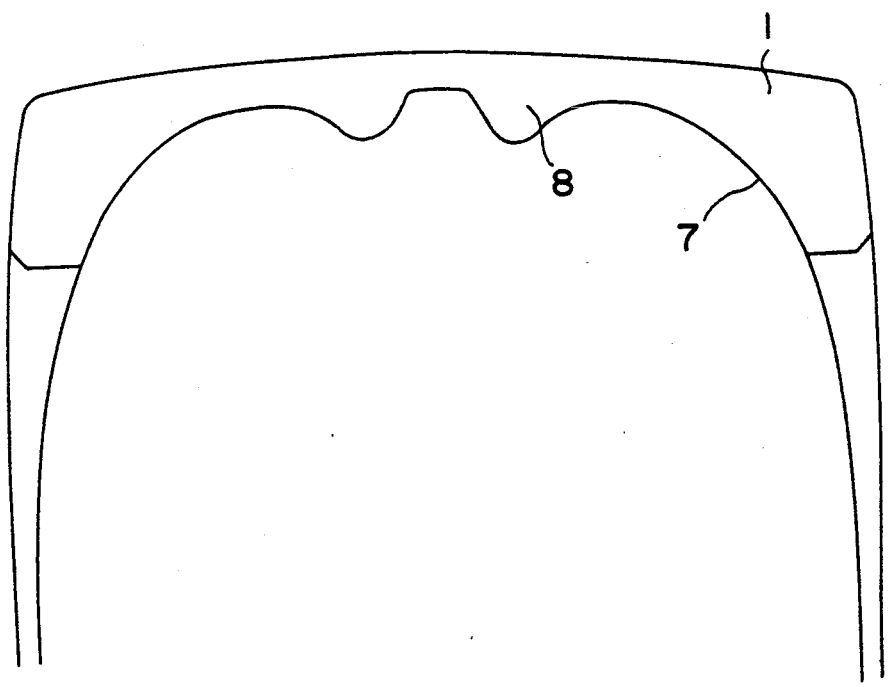
FIG. 3 shows the view of the safety spectacles against laser radiation according to FIG. 1 from below.

As is visible in particular from FIGS. 1, 2, and 3, the frame part (1) is drawn temporally on both sides into the spectacle-wearer's temple area and there forms side shields which can also be designated as temple plates.

As shown in FIG. 2, a top safety shield (6) is integrated with the frame part (1), which safety shield covers the area between the frame and the spectacle-wearer's forehead.

It is visible from FIG. 3 that the bottom part of the frame part (1) is constructed as a safety shield (7) which covers the area between the frame and the spectacle-wearer's face. In this case, it may be advantageous to construct this safety shield (7) in such a way that, for reasons of ventilation, a small gap remains between the spectacle-wearer's face and the shield (7). The bottom shield (7) merges directly into the nose pads (8). These are also integrated in the frame part (1).

As is visible from these figures, the frame part (1) forms in cross section a dish which is open towards the spectacle-wearer's face and in the front surface of which the protective filters are inserted.

Figure 4:
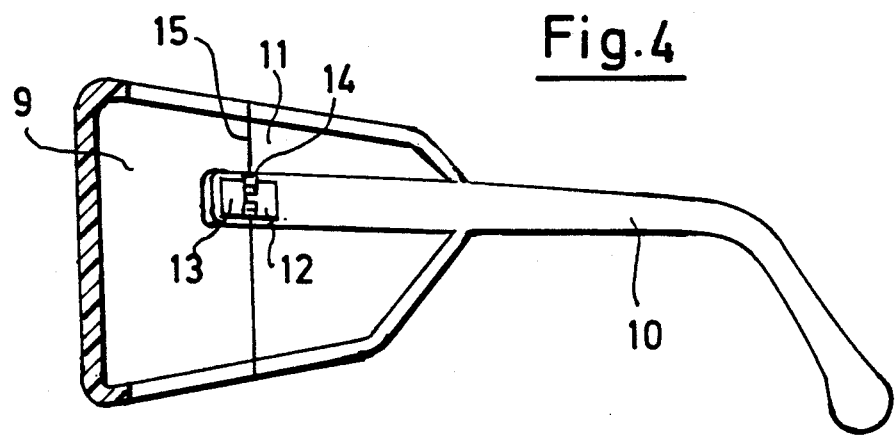
FIG. 4 shows a section along the line IV—IV of FIG. 1.

A side arm (10) is attached rotatably to each temple plate (9). As shown in FIG. 4, the side arm (10) is integrated in a plate (11) which forms the continuation of the temple plate (9). A first hinge part (12) is fixedly connected to the temple plate (11) while the second hinge part (13) is fixedly connected to the plate (9). The hinge pin (14) forms the pivot of the hinge. It is arranged on the inside of the frame (1) and, specifically, in the plane of the separation joint (15) between the two plates (9 and 11).

Figure 5:
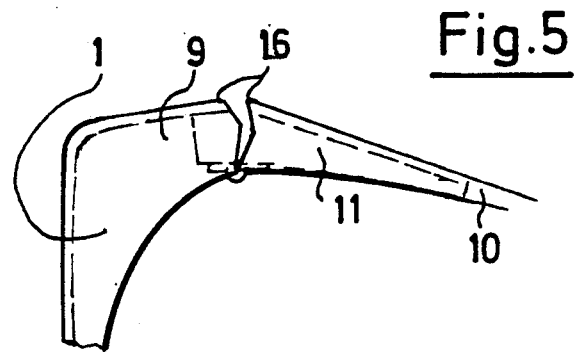
FIG. 5 shows a partial view of the safety spectacles against laser radiation from above with partially folded-in side arm.

As is shown in FIG. 5, the separation joint is constructed in such a way that it contains sloped parts (16) which each extend over the entire wall thickness of the two plates (9 and 11). These two sloping surfaces (16) rest of each other when the side arm is opened. It is achieved by this construction of the separation joint that no gap arises which would allow radiation through even when the side arm is not completely opened.

Figure 6:
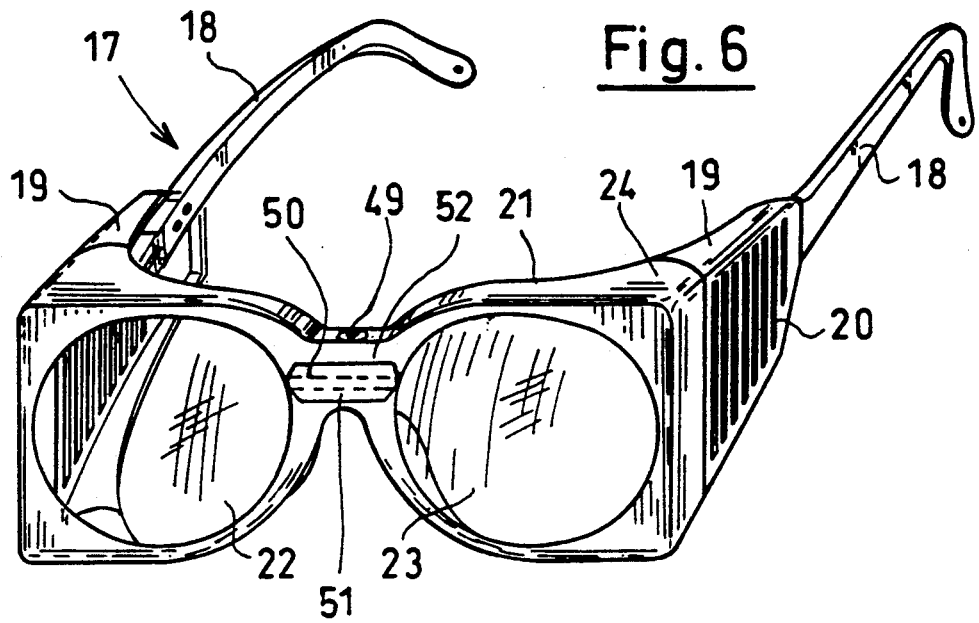
FIG. 6 shows a perspective representation of safety spectacles against laser radiation, with ventilation slits.

The safety spectacles (17) against laser radiation shown in FIG. 6 have on their side arms (18) in each case a plate (19) with ventilation slits (20). These ventilation slits (20) permit a good ventilation in the area between safety spectacles (17) against laser radiation and the spectacle-wearer's face and prevent a build-up of heat underneath the safety spectacles (17) against laser radiation. The protective filters (22, 23) are convexly curved on the object side, in order to reduce the reflected radiation density by divergent reflection. The frame part (21) in the area of the protective filters (22, 23) therefore expediently also has a corresponding curvature. In the frame part (21) there is between the two protective filters (22, 23) a horizontal slit (50), which is necessary for fitting and removing the protective filters (22, 23). Once the protective filters (22, 23) have been fitted into the frame part (21) of the safety spectacles (17) against laser radiation, a covering part (51) is introduced into the slit (50). This covering part (51) is made such that it widens out at the front. A screw (49) goes vertically through the nosepiece (52) and through the slit (50), anchoring the inserted covering part (51) firmly in the slit (50). The exact design on the side arm (18) is shown in the following FIGS. 7–9.

With the exception of the area around the side arms (17), the frame part (21) of the safety spectacles (17) against laser radiation, with the protective filters (22, 23), is designed as described in FIGS. 1–5. The different attachment of the side arms (17) to the temple plate (24) of the frame part (21) is explained in more detail with reference to FIGS. 10 and 11.

Figure 7:
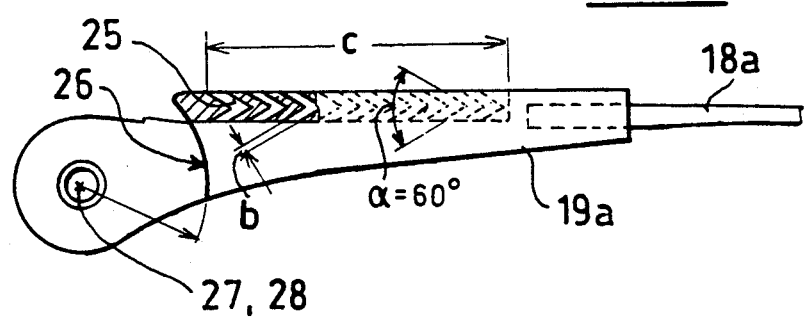
FIG. 7 shows a side arm with ventilation slits, in section.

In FIG. 7, a side arm (18a), which has ventilation slits (25) made in the side of the plate (19a) attached to it, is shown. These ventilation slits (25) have a width (b) and are designed in the form of a V with an included angle $\alpha = 60°$. It is ensured by the V shape of the ventilation slits (25) that no light radiation can penetrate through the ventilation slits (25). The ventilation slits (25) consequently represent a light trap. In this arrangement, they are restricted to one area (c) of the plate (19a). The plate (19a) on the side are (18a) ends on the hinge side with a rounded surface (26), the center of radius (27) of which coincides with the center of pivoting (28) of the hinge.

Figure 8:
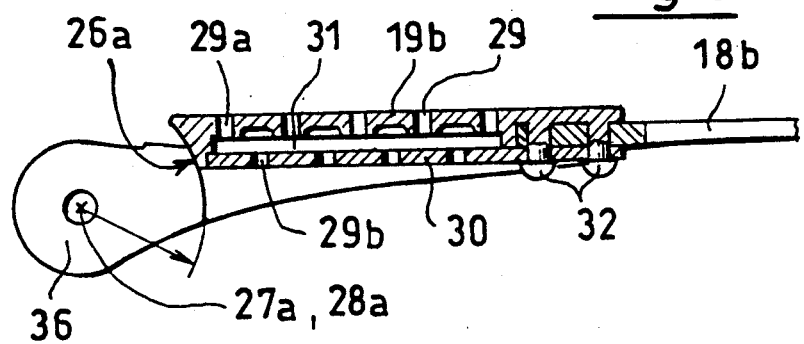
FIG. 8 shows a second side arm with ventilation slits, in section.

It is also the case with the side arm (18b) shown in FIG. 8 that the plate (19a) attached to the side arm (18a) ends on the hinge side with a rounded surface (26a), the center of radius (27a) of which coincides with the center of pivoting (28a) of the hinge. The plate (19a) attached to the side arm (18a) has both outer (29a) and inner (29b) ventilation slits (29). The outer and inner ventilation slits (29) are located both on the plate (19a) attached to the side arm (18a) and on a separate second plate (30) and are connected to one another by a ventilation duct (31). In this arrangement, the outer and inner ventilation slits (29a, b) are mutually arranged in such a way that a light beam cannot fall directly from the outside to the inside through the ventilation slits (29). The plate (19b) attached to the side arm (18b) has on the rear end two elements which can be used as rivets (32). With these rivets (32), both the second separate plate (30) and the side arm (18b) are attached to the plate (19b).

In FIG. 9, a side arm (18b) with plate (19b) attached to it and ventilation slits (29a, b) according to FIG. 8 are shown in side view from the inside with a split nosepiece (34) on the frame part (33) of the safety spectacles (35) against laser radiation. It can be clearly seen here that the outer and inner ventilation slits (29a, b) are arranged mutually offset.

The plate (19b) has two hinge parts (36 and 36a, b). With these hinge parts (36), the side arm (18b) is pivotably attached in the upper and lower area of the temple plate (48a, b). This is performed by two screws (37a, b), the thread of which only grips in one threaded bore in each case in the temple plate (48a, b). There is a distance (d) between the two hinge parts (36).

In FIG. 10, the side arm (18b) with plate (19b) attached to it from FIGS. 8 and 9 is shown in a view from above. The curvilinear sliding surface (38) between the plate (19b) on the side arm (18b) and the temple plate (39) of the frame part (33) has its center of radius (40) at the center of pivoting (28a) of the pivot hinge. Since the temple plate (39) has a thickening (39a) in the vicinity of the sliding surface (38), the side arm (18b) can be moved as far as the position (18b') without radiation being able to penetrate in the area of the sliding surface (38). In the position (18b''), the safety spectacles against laser radiation are in their storing position. Should it be necessary that the side arm (18b) can be moved beyond the position (18b') shown in FIG. 10 without light radiation on the sliding surface (38) being able to penetrate into the interior of the spectacle frame, the thickening (39a) can also be increased. This is shown in FIG. 11.

In FIG. 11, the spectacle arm (46) can also be moved out beyond the position (46') without light radiation being above to penetrate into the interior of the safety spectacles (45) against laser radiation. The safety spectacles (45) against laser radiation have a lip-like extension (44) on the sliding surface (43), the center of radius (41) of which here again is at the center of pivoting (42) of the pivot hinge. The plate (47) of the side arm (46) can slide along this lip-like extension (44). In this arrangement, the extension (44) is located in the area (d) between the two hinge parts (36a, b in FIG. 9) on the plate (47). In its storing position (46''), the safety spectacles (45) against laser radiation can be inserted into their case (not shown here).

The new safety spectacles against laser radiation illustrated in the figures can, for example, be produced from aluminum. It is also possible to construct the frame from a plastic, preferably from the plastic available under the trade name "Grilamid". In this case, the frame part is expediently formed from glass fiber reinforced plastic, while the side arms and the integrated plate are formed from plastic which is not glass fiber reinforced. Furthermore, it is advantageous to provide the side arms with a metal insert in a manner not illustrated here in order to keep them deformable to a certain extent so that the frame can be adapted exactly to the spectacle-wearer's head.

The configuration of the ventilation slits shown in FIGS. 7 and 8 is only by way of example. All configurations of ventilation slits which prevent a direct penetration of light radiation can be used.

We claim:

1. Safety spectacles to use in an area with laser radiation, the spectacles comprising protective filters for protecting the eyes against laser radiation, a spectacle frame serving to accommodate said protective filters and moveable side arms, wherein said frame is of integral construction and has in one cross section the form of a dish that is open towards a spectacle wearer's face, said frame has an inner, a front, a top and a bottom surface, said protective filters are inserted in said front surface of said frame, said top and said bottom surfaces substantially cover the entire area as far as the spectacle wearer's face, said frame has sides that extend temporally into the spectacle wearer's temple area, said sides form a temple plate in each case, said temple plate has an inside and a first hinge part attached on said inside for pivotable attachment of one of said side arms, each of said side arms has a side arm plate, said side arm plate has an inside and forms a continuation of said temple plate when said side arm is at least partly open, said temple plate and said side arm extend to the spectacle wearer's face, each of said side arms has an end portion facing said temple plate, and a second hinge part, pivotable with said first hinge part, is integrated in said inside of said end portion of said side arm plate.

2. Safety spectacles as claimed in claim 1, wherein said temple plate and said side arm plate are separated at a separation joint and have walls at said separation joint with surfaces sloped over an entire wall thickness in such a way that said sloping surfaces rest on each other when said side arm is substantially open.

3. Safety spectacles as claimed in one of claims 1 or 2, wherein each of said side arms is provided with a metal insert.

4. Safety spectacles as claimed in one of claims 1 or 2, wherein ventilation slits are provided is said side arm plate.

5. Safety spectacles as claimed in claim 4, wherein said ventilation slits are impermeable to light radiation.

6. Safety spectacles as claimed in one of claims 1 or 2, wherein said hinge parts have a pivot point that lies inside of said separation joint.

7. Safety spectacles as claimed in claim 2, wherein said hinge parts have a center of pivoting and said sloping surfaces comprise curvilinear sliding surfaces with a center of radius that coincides with said center of pivoting, and said hinge parts are provided between said side arm plate and said spectacle frame.

8. Safety spectacles as claimed in claim 7, wherein said center of pivoting is located in the area of said temple plate.

9. Safety spectacles as claimed in one of claims 1 or 2, wherein said second hinge part comprises two hinge members formed on said inner side of said side arm plate for attaching said side arm plate to said temple plate.

10. Safety spectacles as claimed in claim 9, wherein said hinge members are arranged in upper and lower areas of said side arm plate.

11. Safety spectacles as claimed in claim 8, wherein said spectacle frame has an interior, and a lip-like extension is formed in said frame interior in the region of said sloping surface in space not covered by said hinge parts.

12. Safety spectacles as claimed in claim 9, wherein said spectacle frame has an interior, and a lip-like extension is formed in said frame interior in the region of said inner side of said side arm plate in space not covered by said hinge parts.

13. Safety spectacles to use in an area with laser radiation, the spectacles comprising protective filters for protecting the eyes against laser radiation, a spectacle frame serving to accommodate said protective filters and moveable side arms, wherein said frame is of integral construction and has in one cross section the form of a dish that is open towards a spectacle wearer's face, said frame has an inner, a front, a top and a bottom surface, said protective filters are inserted in said front surface of said frame, said top and said bottom surfaces cover an area as far as the spectacle wearer's face, said frame has sides that extend temporally into the spectacle wearer's temple area, said sides form a temple plate in each case, said temple plate has an inside and a first hinge part attached on said inside for pivotable attachment of one of said side arms, each of said side arms has a side arm plate, said side arm plate has an inside and forms a continuation of said temple plate when said side arm is at least partly open, each of said side arms has an end portion facing said temple plate, a second hinge part, pivotable with said first hinge part, is integrated in said inside of said end portion of said side arm plate, and said temple plate and said side arm plate are separated at a separation joint and have walls at said separation joint with surfaces sloped over an entire wall thickness in such a way that said sloping surfaces rest on each other when said side arm is substantially open.

14. Safety spectacles to use in an area with laser radiation, the spectacles comprising protective filters for protecting the eyes against laser radiation, a spectacle frame serving to accommodate said protective filters and moveable side arms, wherein said frame is of integral construction and has in one cross section the form of a dish that is open towards a spectacle wearer's face, said frame has an inner, a front, a top and a bottom surface, said protective filters are inserted in said front surface of said frame, said top and said bottom surfaces cover an area as far as the spectacle wearer's face, said frame has sides that extend temporally into the spectacle wearer's temple area, said sides form a temple plate in each case, said temple plate has an inside and a first hinge part attached on said inside for pivotable attachment of one of said side arms, each of said side arms has a side arm plate, said side arm plate has an inside and forms a continuation of said temple plate when said side arm is at least partly open, each of said side arms has an end portion facing said temple plate, a second hinge part, pivotable with said first hinge part, is integrated in said inside of said end portion of said side arm plate, said hinge parts have a center of pivoting and said sloping surfaces comprise curvilinear sliding surfaces with a center of radius that coincides with said center of pivoting, and said hinge parts are provided between said side arm plate and said spectacle frame.

15. Safety spectacles as claimed in claim 14, wherein said center of pivoting is located in the area of said temple plate.

* * * * *